(12) United States Patent
Masada et al.

(10) Patent No.: US 12,385,800 B2
(45) Date of Patent: Aug. 12, 2025

(54) LIGHT IRRADIATION DEVICE

(71) Applicant: Ushio Denki Kabushiki Kaisha, Tokyo (JP)

(72) Inventors: Kohei Masada, Tokyo (JP); Yoshihiro Kanahashi, Tokyo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 655 days.

(21) Appl. No.: 17/794,211

(22) PCT Filed: Dec. 3, 2020

(86) PCT No.: PCT/JP2020/045055
§ 371 (c)(1),
(2) Date: Jul. 20, 2022

(87) PCT Pub. No.: WO2021/149367
PCT Pub. Date: Jul. 29, 2021

(65) Prior Publication Data
US 2023/0052579 A1    Feb. 16, 2023

(30) Foreign Application Priority Data
Jan. 24, 2020  (JP) ................. 2020-009735

(51) Int. Cl.
*G01M 3/38*    (2006.01)

(52) U.S. Cl.
CPC .................... *G01M 3/38* (2013.01)

(58) Field of Classification Search
CPC ........ G01M 3/38; G01M 3/186; H10H 20/80; H10H 20/858; A61L 2/10
USPC ........................................... 210/600
See application file for complete search history.

(56) References Cited

FOREIGN PATENT DOCUMENTS

JP    2017-143971 A    8/2017

*Primary Examiner* — Ekandra S. Miller-Cruz
(74) *Attorney, Agent, or Firm* — Yoshida & Associates LLC; Kenichiro Yoshida

(57) ABSTRACT

Provided is a light irradiation device capable of safely detecting liquid leakage in the occurrence of the liquid leakage. A light irradiation device includes a light-emitting element, a cylindrical light source supporter having an outer wall surface on which the light-emitting element is disposed, a flow groove formed on the outer wall surface in an axial direction of the light source supporter, a reservoir that is communicated to the flow groove at a first end of the light source supporter in the axial direction and that is configured to allow liquid to be stored, and a detector configured to detect the liquid stored in the reservoir. The first end of the light source supporter is located at a position downward in the vertical direction relative to a second end of the light source supporter, the reservoir being disposed at the first end in the axial direction thereof.

14 Claims, 9 Drawing Sheets

LIGHT IRRADIATION DEVICE

TECHNICAL FIELD

The present invention relates to a light irradiation device, particularly relates to the light irradiation device in which light is radiated by a light-emitting element.

BACKGROUND ART

As a light source for sterilization and photochemical treatment of fluids in containers and tanks, a light irradiation device is known, as disclosed in Patent Document 1 below, such as a long light irradiation device extending in one direction and provided with a plurality of LEDs as a light source.

CITATION LIST

Patent Documents

Patent Document 1: JP-A-2017-143971

SUMMARY OF INVENTION

Technical Problem

The present inventors have studied such a light irradiation device as described above for use in sterilization and photochemical treatment of fluids in containers and tanks, then have found that the light irradiation device has a problem as described below.

LEDs emit light and generate heat when power is supplied, and their temperature gradually rises. However, since the luminous efficiency of LEDs decreases as their temperature rises, most light irradiation devices that use LEDs as a light source are provided with a cooling mechanism.

For example, in a rod-shaped, long light irradiation device such as the light irradiation device disclosed in Patent Document 1 above, a cooling medium is provided to allow a cooling medium to flow through a channel formed inside the light source supporter on which LEDs as a light source is mounted.

In a light source supporter the inside of which a cooling medium flows through, the cooling medium may occasionally leak out of the light source supporter. In particular, in a case in which a long light source supporter is formed by connecting multiple members in its axial direction, connection sections are formed at regular intervals in the axial direction. Such connections sections are not completely fixed with, for example, adhesives, for their transportation and maintenance work; however they are treated for liquid leakage prevention with, for example, rubber O-rings, so as to prevent the cooling medium that flows through the interior from leaking onto the outer wall surface.

However, even when the liquid leakage prevention is treated using O-rings or other means, it is difficult to completely seal the gap between the connection sections, making it difficult to completely prevent the cooling medium that flows through the light source supporter from leaking. In addition, the liquid leakage prevention using the O-ring results in functioning less due to deterioration over time and other factors. If the cooling medium leaks onto the outer wall surface while power is being supplied to LEDs, short circuit in the wirings that supply power to the LEDs may occur, resulting in damage to the LED elements, the wiring substrates, and the light irradiation device itself.

In view of the above issues, it is an object of the present invention to provide a light irradiation device capable of safely detecting liquid leakage in the occurrence of the liquid leakage.

Solution to Problem

A light irradiation device of the present invention includes
a light-emitting element;
a cylindrical light source supporter having an outer wall surface on which the light-emitting element is disposed, and including a channel that is formed inside the light source supporter to allow cooling medium to flow through;
a flow groove that is formed on the outer wall surface in an axial direction of the light source supporter;
a reservoir that is communicated to the flow groove at a first end of the light source supporter in the axial direction and that is configured to allow liquid to be stored; and
a detector that is configured to allow the liquid stored in the reservoir to be detectable,
wherein the first end of the light source supporter is located at a position downward in the vertical direction relative to a second end of the light source supporter, the reservoir being disposed at the first end in the axial direction thereof.

The light-emitting element is preferably an LED that emits ultraviolet light over a wide area as an element to perform sterilization and photochemical treatment on the object to be treated; however other types of the light-emitting element such as a LD may be used. Other components such as phosphor may be mounted among the light-emitting elements. In addition, each light-emitting element may be a light-emitting element that emits light other than ultraviolet light such as visible light and infrared light. For example, when the light-emitting element is an LED emitting infrared light, the above light irradiation device can perform heating treatment on the object to be treated.

The cooling medium flowing inside the light source supporter is a liquid, such as water.

When part of the cooling medium flowing inside the light source supporter leaks onto the outer wall surface thereof, the cooling medium flows along the flow groove formed on the outer wall surface toward the reservoir by its own weight. The cooling medium flows along the flow groove formed on the outer wall surface of the light source supporter and is guided to the reservoir in a manner to keep away from, for example, a wiring pattern that supplies power to the light-emitting elements formed on the outer wall surface of the light source supporter. When the cooling medium reaches the reservoir, the detector detects that the cooling medium, which is a liquid, has been stored in the reservoir.

Hence, the above configuration is capable of safely detecting the leakage of the cooling medium flowing through the inside of the light source supporter. Furthermore, based on the signal indicating that the detector has detected the liquid, the configuration is capable of configuring a system that controls the supply of power to the light-emitting element to be immediately stopped or controls the removal operation of the light irradiation device to be started. Configuring the system can provide a mechanism to prevent the light irradiation device from being damaged, or a mechanism to avoid sparks or electrical discharges caused by a short circuit in the wiring pattern or the like, which may result in, for example, igniting the object to be treated.

In the above configuration, the first end of the light source supporter provided with reservoir is located lower than the second end thereof in its axial direction; however the axis of the light source supporter is not necessarily positioned in the vertical direction.

In the light irradiation device described above, the detector may include a detection surface that detects the liquid when the liquid is in contact with the detection surface, and the detection surface may be located to face downward in the vertical direction.

For example, if the detection surface of the detector faces upward in the vertical direction, the detector cannot detect a liquid unless the liquid is stored in the reservoir to a position higher than the detection surface. The above configuration allows the detector to detect a liquid even though the amount of the liquid is just small enough to be in contact with the detection surface, regardless of its liquid level, enabling an early detection of liquid leakage.

The above-mentioned light irradiation device may include a plurality of substrates on the outer wall surface, the light-emitting element being mounted on the substrates, and the flow groove may be formed between the substrates that are adjacent each other in a circumferential direction of the light source supporter.

In many cases, the light source supporter is provided with the substrate with a wiring pattern on the outer wall surface thereof, the light-emitting element being mounted on the substrate. The plurality of substrates are arranged on the light source supporter so as to adjust the light intensity and the shape of the light source supporter.

The above configuration allows the cooling medium, which is a liquid, to flow through a slit where the substrates are not located toward the reservoir without adhering to the wiring patterns or the like, formed on the substrates. Therefore, the liquid leakage can be detected more safely.

In the above-mentioned light irradiation device, the plurality of flow grooves may be formed in the circumferential direction when viewed in the axial direction of the light source supporter.

For example, in the case in which only one flow groove is configured on the outer wall surface of the light source supporter, if a leakage of cooling medium occurs at a position opposite to the flow groove with respect to the axis of the light source supporter when viewed from its axial direction, the cooling medium leaking onto the outer wall surface of the light source supporter needs to travel halfway around the outer wall surface of the light source supporter in a circumferential direction to reach the flow groove. Hence, the cooling medium may be assumed to adhere to the wiring pattern or the light-emitting element before reaching the flow groove, or flow on the outer wall surface toward the reservoir without reaching the flow groove.

Hence, even if a leakage of the cooling medium occurs, configuring the plurality of flow grooves in the circumferential direction of the light source supporter is capable of reliably guiding the leaked liquid to the reservoir through the flow groove formed at a location closest to that at which the leakage occurs. Therefore, this configuration further reduces a risk of the leaked liquid adhering to the wiring pattern and light-emitting element formed on the substrate, enabling the safe detection of the liquid leakage.

The plurality of flow grooves may be formed at equal intervals in the circumferential direction when viewed in the axial direction of the light source supporter.

In the above configuration, the cooling medium that leaks onto the outer wall surface of the light source supporter is likely to reach one of the flow grooves, flowing toward the reservoir more safely and reliably.

In the light irradiation device described above, the reservoir may include a receiving portion having a cylindrical shape with an inner bottom, the receiving portion being configured to cover the first end of the light source supporter in the axial direction.

The above configuration allows the leaked liquid that has flowed through the flow groove to flow toward the reservoir without splashing.

The light irradiation device of the present invention may be immersed at least partially in a liquid to be photochemically treated, and may be used to irradiate the liquid with light radiated from the light-emitting element mounted on the outer wall surface of the light source supporter, from inside the liquid.

In the above light irradiation device, the reservoir may include a tubular body that is transmissive to light and covers the light source supporter.

The above configuration, in which the tubular body serves to protect the light source supporter, enables the light irradiation device of the present invention to be immersed in the liquid to be photochemically treated.

Furthermore, in the above light irradiation device, the light source supporter may be connected to a member that is deformable to the detector in the axial direction.

The above configuration can mitigate an impact on the protective tube to avoid damage on the protective tube, if the light source supporter is made to accidentally hit the reservoir at the end opposite to the opening of the protective tube when inserted inside the protective tube. In addition, the configuration enables the detection surface of the detector to be disposed to be in contact with or proximity to the surface of the reservoir, as well as enables the position of the light source supporter to be adjusted to a desired position in the axial direction.

The above light irradiation device may include a protective tube that is transmissive to light, and that accommodates the light source supporter; and the reservoir may include a communication hole that communicates a space in which the liquid is stored with a space inside the protective tube.

The above configuration enables the light irradiation device of the present invention to be immersed in the liquid to be treated when the object to be photochemically treated is a liquid, and thus irradiate the object with light from inside the liquid to be treated. Hence, the above configuration enables the light irradiation device to irradiate even the liquid to be treated that is stagnant in the central side of the container with light, the central side of the container being a region that light by the irradiation from the side or the top of the container is less likely to reach, thus suppressing uneven irradiation and shortening the treatment time.

Furthermore, in the above configuration, if the protective tube is damaged while being immersed in the liquid to be treated and the liquid enters the protective tube, for example, the liquid flows along the outer wall of the protective tube toward the bottom of the protective tube. When a certain amount of the liquid is stored at the bottom of the protective tube, the liquid flows through the communication hole toward the inside of the reservoir, flows into the reservoir, and is detected by the detector. Hence, this configuration is capable of detecting the liquid when the liquid leaks into the inside of the protective tube due to the damage of the protective tube.

Advantageous Effects of Invention

The present invention provides a light irradiation device that is capable of safely detecting liquid leakage when the liquid leakage occurs.

DESCRIPTION OF EMBODIMENTS

Figure 1:
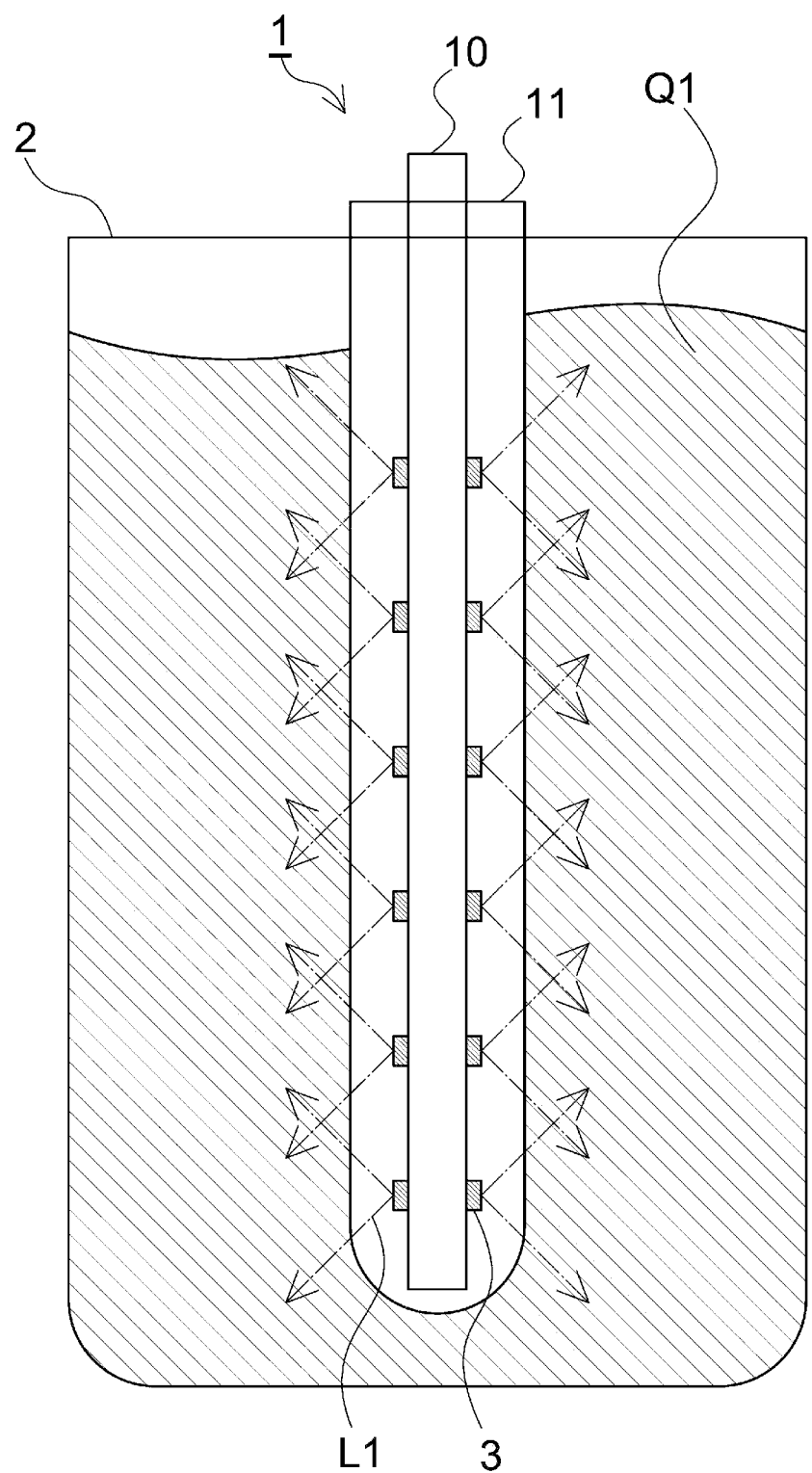
FIG. 1 is a drawing schematically illustrating an example of a use mode of a light irradiation device.

Hereinafter, embodiments of a light irradiation device according to the present invention will be described with reference to the drawings. Each of the following drawings is schematically illustrated, and the dimensional ratios and numbers in the drawings do not necessarily correspond to the actual dimensional ratios and numbers.

[Use Mode]

FIG. 1 is a drawing schematically illustrating an example of a use mode of a light irradiation device 1. As shown in FIG. 1, the light irradiation device 1 of the present invention includes a light source supporter 10 and a protective tube 11. The light source supporter 10 is rod-shaped and long, and is provided with a plurality of LEDs 3, which are light-emitting elements, on the outer wall surface thereof. Liquid to be treated Q1 that is stored in a container 2 and an object to be treated, is irradiated with ultraviolet light L1 emitted from the LEDs 3, and thus the liquid to be treated Q1 is sterilized or photochemically treated.

As shown in FIG. 1, the light irradiation device 1 of the present invention, which is provided with the protective tube 11, is capable of being immersed in the liquid to be treated Q1 in the container 2. The light irradiation device 1 being immersed in the liquid to be treated Q1, and irradiating the liquid to be treated Q1 with the ultraviolet light L1 emitted from the LEDs 3 from inside the liquid to be treated Q1, makes it possible to effectively irradiate the liquid to be treated Q1 with the ultraviolet light L1, performing sterilization and photochemical treatment.

The use mode shown in FIG. 1 is an example and does not limit the use mode of the light irradiation device 1. For example, the light irradiation device 1 may be provided with no protective tube 11, and used in a configuration in which it is not immersed in the liquid to be treated Q1. Even with the configuration, if a liquid leakage of a cooling medium circulating inside the light source supporter occurs, for example, the liquid leakage can be safely detected.

Hereinafter, the configuration of the light irradiation device 1 will be described in detail below.

Figure 2:
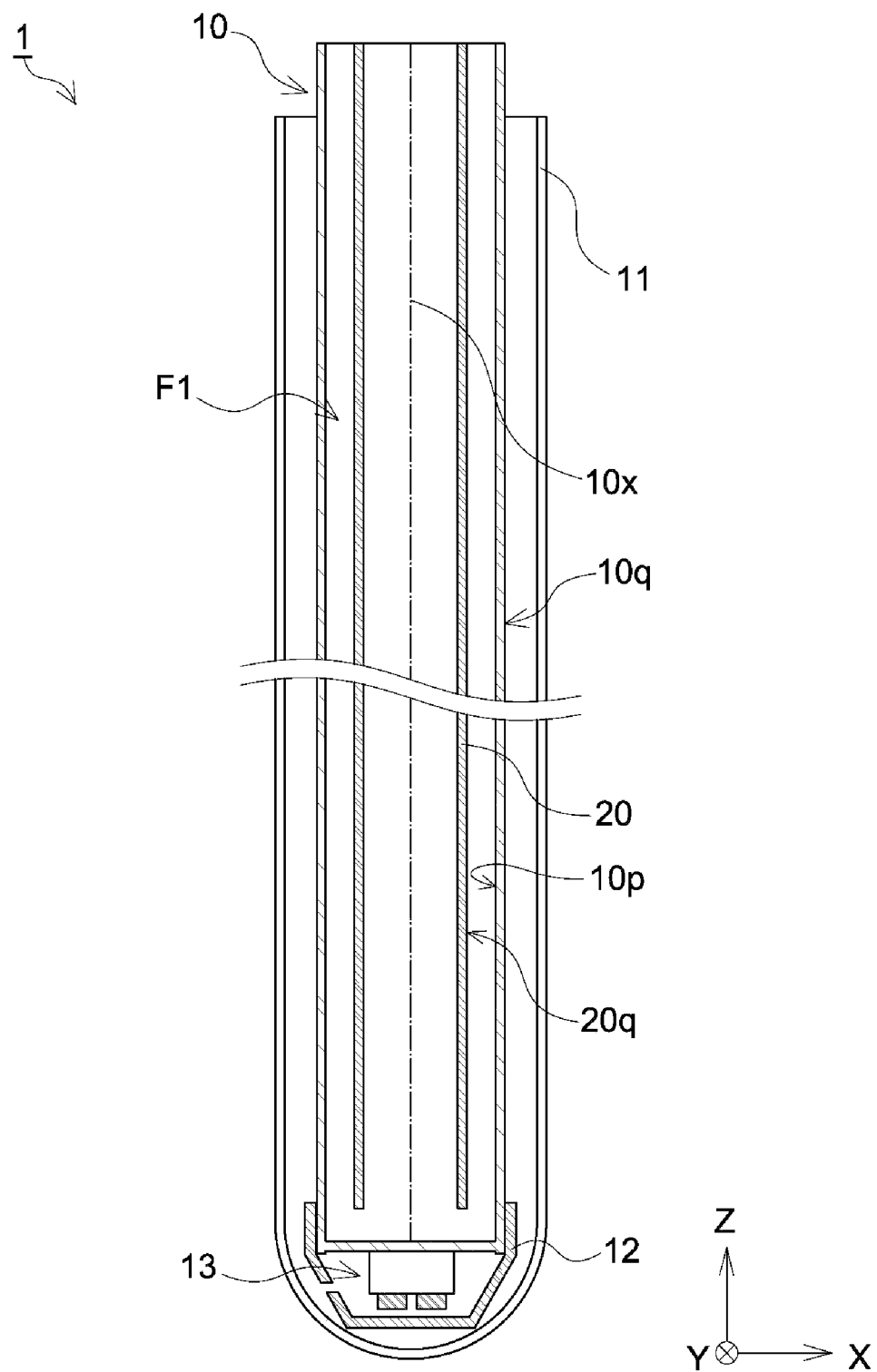
FIG. 2 is a cross-sectional view schematically illustrating an overall configuration of an embodiment of the light irradiation device.

FIG. 2 is a cross-sectional view schematically illustrating an overall configuration of an embodiment of the light irradiation device 1. In the following description, a direction of an axis 10x of the light source supporter 10 is denoted as a Z direction, and a plane orthogonal to the Z direction is a XY plane. When a direction is expressed to distinguish between positive and negative directions, a positive or negative sign is added to the direction, such as "+Z direction" and "−Z direction", and when a direction is expressed without distinguishing between positive and negative directions, it is simply described as "Z direction".

Figure 3:
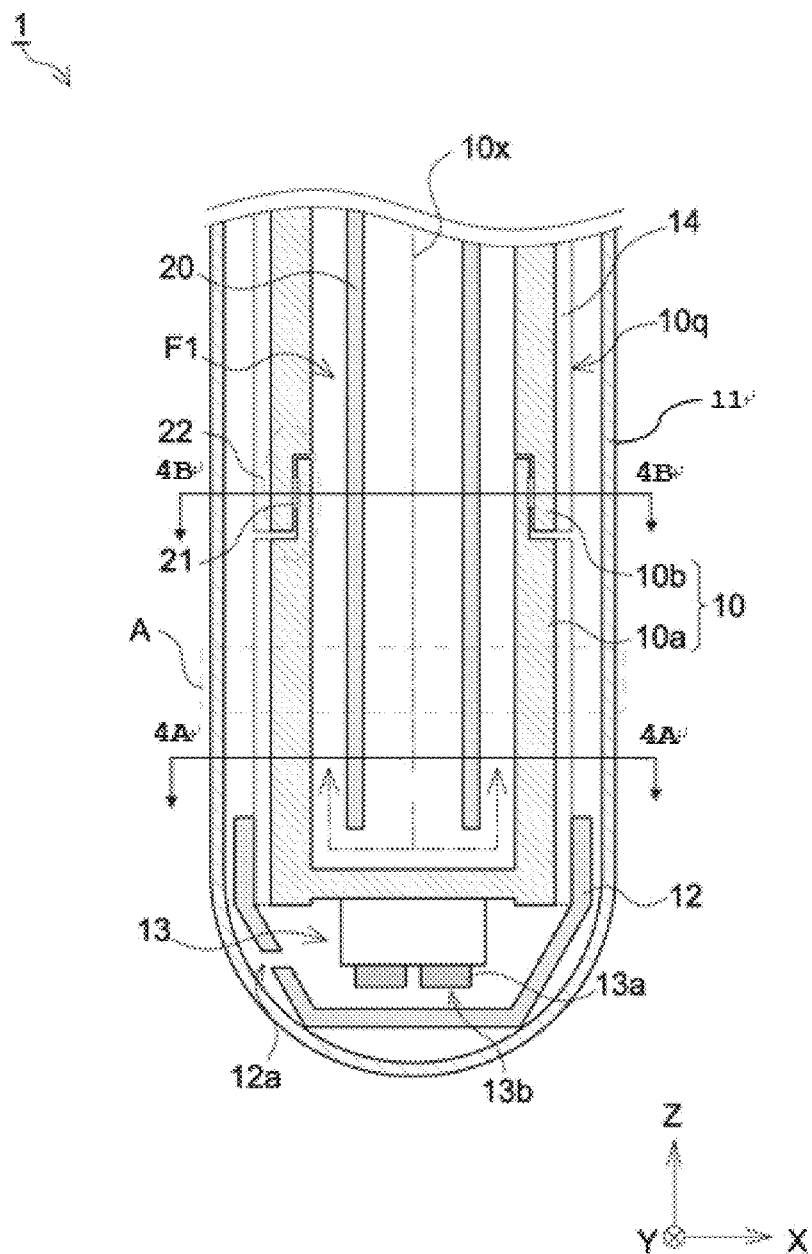
FIG. 3 is a cross-sectional view schematically illustrating the embodiment of the light irradiation device.
Figure 4A:
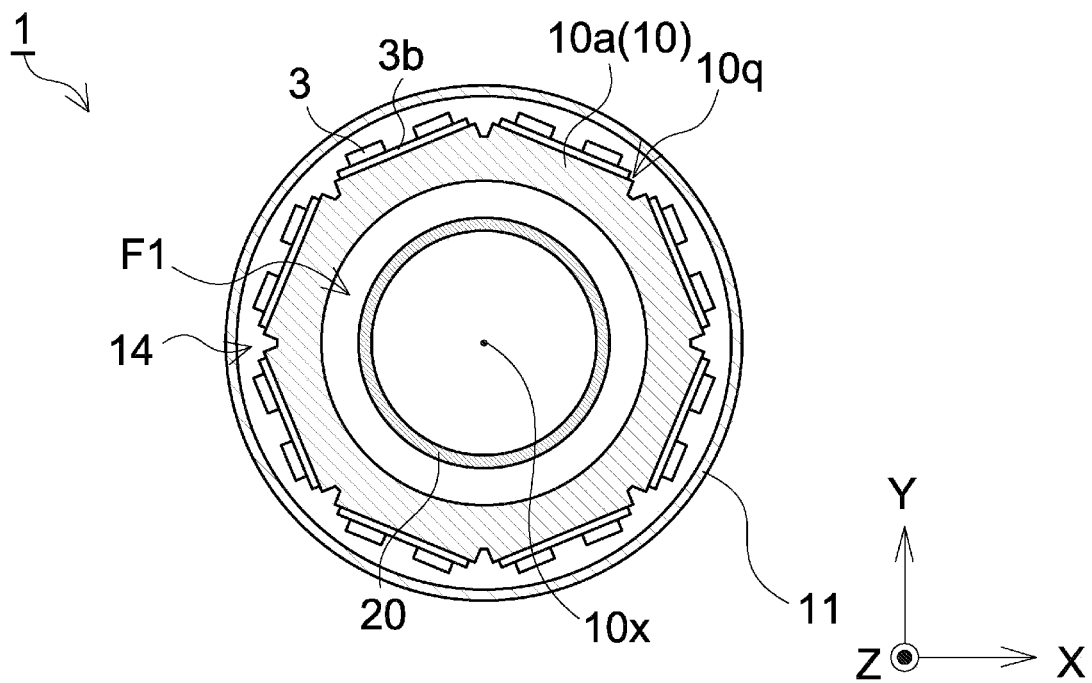
FIG. 4A is a cross-sectional view of the light irradiation device taken along the line 4A-4A of FIG. 3.
Figure 4B:
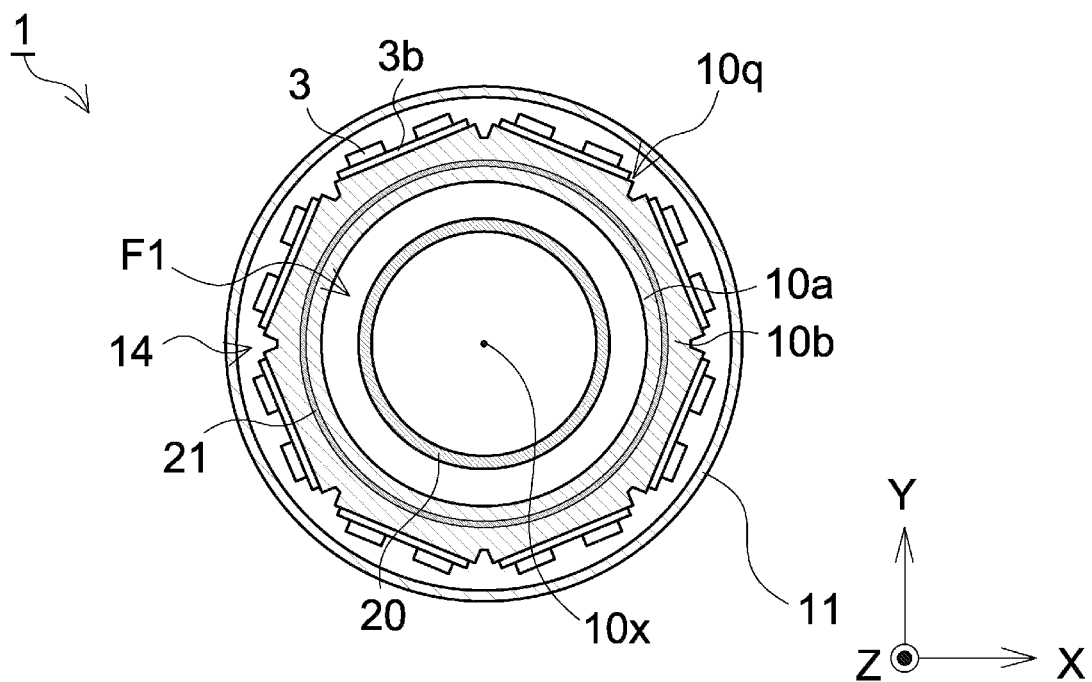
FIG. 4B is a cross-sectional view of the light irradiation device taken along the line 4B-4B of FIG. 3.

FIG. 3 is a schematic cross-sectional view of an embodiment of the light irradiation device 1. FIG. 4A is a cross-sectional view of the light irradiation device 1 taken along the line 4A-4A of FIG. 3. FIG. 4B is a cross-sectional view of the light irradiation device 1 taken along the line 4B-4B of FIG. 3. FIG. 4B is a cross-sectional view of the connection section 22 of the light irradiation device 1 in FIG. 3 when cut in a plane perpendicular to the Z direction. As shown in FIGS. 2 to 4B, the light irradiation device 1 has a light source supporter 10 and a protective tube 11, the light source supporter 10 has a reservoir 12 on the first end side (−Z side) in the axial direction (Z direction) 2 and a detector 13 inside the reservoir 12, and on the outer wall surface $10q$, a flow groove 14 is formed on the outer wall surface $10q$.

The light source supporter 10 has a cylindrical shape, as shown in FIGS. 3, 4a and 4b, and has an outer wall surface $10q$ provided with substrates $3b$ on which the LEDs 3, which are light-emitting elements that emit ultraviolet light L1, are mounted. The substrates $3b$ have wiring patterns (not shown in the figure) formed to supply power to the LEDs 3. The wiring patterns are connected to conductive plates or wirings in a manner that distribute power supplied from a power supply unit through the respective substrates $3b$, and that are apart from above the outer wall surface $10q$ and the outer wall surface $10q$.

As shown in FIG. 1, the protective tube 11 is provided in the light irradiation device 1, for example, when the light irradiation device 1 is immersed in liquid to be treated Q1. As shown in FIGS. 3, 4A and 4B, the protective tube 11 accommodates the light source supporter 10 thereinside and protects the light source supporter 10 so as to prevent the liquid to be treated Q1 from adhering to the LEDs 3 and the substrates $3b$ that are mounted on the outer wall surface $10q$ of the light source supporter 10, thereby avoiding, for example, a short circuit in the wirings.

The protective tube 11 is formed of a material that is transmissive to light and capable of being immersed in the liquid to be treated Q1. The term "transmissive to light" as used herein means that the material has transmittance of at least 70% with respect to light having a wavelength band used for treating the object to be treated, and does not necessarily have high transmittance to visible light. Examples of the material constituting the protective tube 11 may include quartz glass or borosilicate glass.

The reservoir 12 is, as shown in FIG. 3, a receiving section that covers the first end of the light source supporter 10 in the Z-direction and has a cylinder shape with an inner bottom. The reservoir 12 is provided with a communication hole $12a$ that connects a space for storing liquid to a space inside the protective tube 11, so that the liquid that has been stored inside the protective tube 11 flows into the reservoir 12.

The detector 13 is provided with two electrodes 13a, as shown in FIG. 3, with the detection surfaces 13b facing the −Z direction (downward in the vertical direction). When the liquid stored in the reservoir 12 comes into contact with both of the detection surfaces 13b, a current is generated between the detection surfaces 13b via the liquid, and thus the detector 13 is configured to detect the liquid stored therein.

As shown in FIGS. 3, 4A and 4B, the plurality of flow grooves 14 are formed on the outer wall surface 10q along the axis 10x of the light source supporter 10, between the substrates 3b adjacent to each flow groove 14, and at equal intervals in the circumferential direction of the light source supporter 10 so as to communicate with the reservoir 12.

A cylinder 20 is disposed inside the light source supporter 10 to form a channel F1 through which a cooling medium for cooling the LEDs 3 is cooled is allowed to pass. As shown in FIGS. 2 and 3, the channel F1 is positioned to align the axis 10x of the light source supporter 10 with the axis of the cylinder 20. The channel F1 includes an outward path inside the cylinder 20 through which the cooling medium flows from the end of the +Z side toward the end of the −Z side and a return path through which the cooling medium flows from the end of the −Z side toward the end of the +Z side, the return path being between an outer wall surface 20q of the cylinder 20 and an inner wall surface 10p of the light source supporter 10. The cooling medium is a liquid passed through the channel F1 to cool the LEDs 3, such as water.

The cylinder 20 is disposed apart from the end of the −Z side of the light source supporter 10, thus allowing the outward path of the channel F1 to be communicated with the return path thereof at the end of the −Z side. Hence, the cooling medium injected inside the cylinder 20 from the end of the +Z side of light source supporter 10 flows through the outward path inside the cylinder 20, as shown by the arrow in FIG. 3, communicates with the return path at the end of the −Z side, and passes through the return path between the outer wall surface 20q of the cylinder 20 and the inner wall surface 10p of the light source supporter 10, and drains away outside the light source supporter 10 at the end of the +Z side.

The light source supporter 10 of the first embodiment is configured to connect a plurality of connection members (10a, 10b) together to form the connection section 22. As shown in FIGS. 3 and 4B, the connection section 22 of the first embodiment is formed in a manner that the convex part of the one connection member 10a is inserted into the concave part of the other connection member 10b.

An O-ring 21 is mounted between the connection members (10a, 10b) to seal a gap therebetween so as to prevent the leakage of the cooling medium that flows through the inside of the light source supporter 10. The light source supporter 10 may be provided with the connection section 22 configured to be formed with a single member in order to prevent the leakage of the cooling medium flowing through the inside thereof.

In order to be capable of detecting even a small amount of liquid stored in the reservoir 12, the detection surface 13b is preferably positioned to make a distance between the detection surface 13b and the reservoir 12 to be as close as possible; the distance is, for example, within 5 mm.

The light source supporter 10 of the first embodiment has its axis 10x positioned in the vertical direction; however, the light source supporter 10, if the first end of the light source supporter 10 in which the reservoir 12 is disposed is positioned downward in the vertical direction relative to the second end thereof, may have its axis 10x positioned non-parallel to the vertical direction.

Hereinafter, the occurrence and detection of liquid leakage will now be explained with reference to the drawings.

Figure 5A:
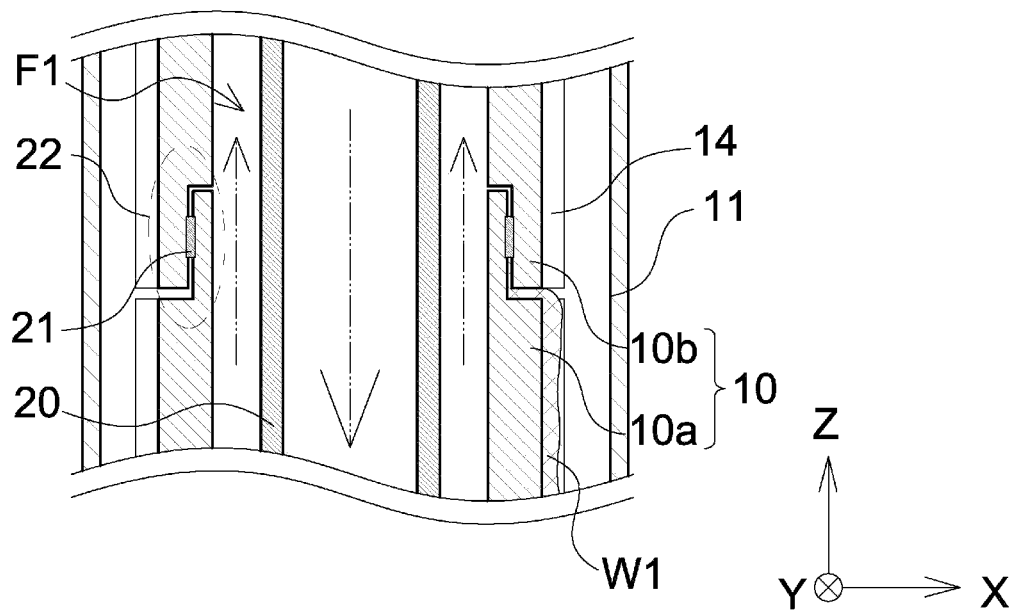
FIG. 5A is an enlarged view of the connection section of the light irradiation device of FIG. 3.

First, described is the case in which the cooling medium flowing through the channel F1 inside the light source supporter 10 leaks at the connection section 22 to the outside of the light source supporter 10. FIG. 5A is an enlarged view of the connection section 22 of the light irradiation device 1 in FIG. 3. As shown in FIG. 5A, in the case in which the light source supporter 10 is configured to connect the plurality of connection members (10a, 10b), the deterioration of defect of the O-ring 21, which is mounted to prevent liquid leakage, cause the cooling medium flowing through the channel F1 in the direction of the arrow to leak onto the outer wall surface 10q of the light source supporter 10 as leaked liquid W1.

The leaked liquid W1 leaking onto the outer wall surface 10q of the light source supporter 10 flows along the flow groove 14, which is formed on the outer wall surface 10q of the light source supporter 10, in the −Z direction (downward in the vertical direction).

Figure 5B:
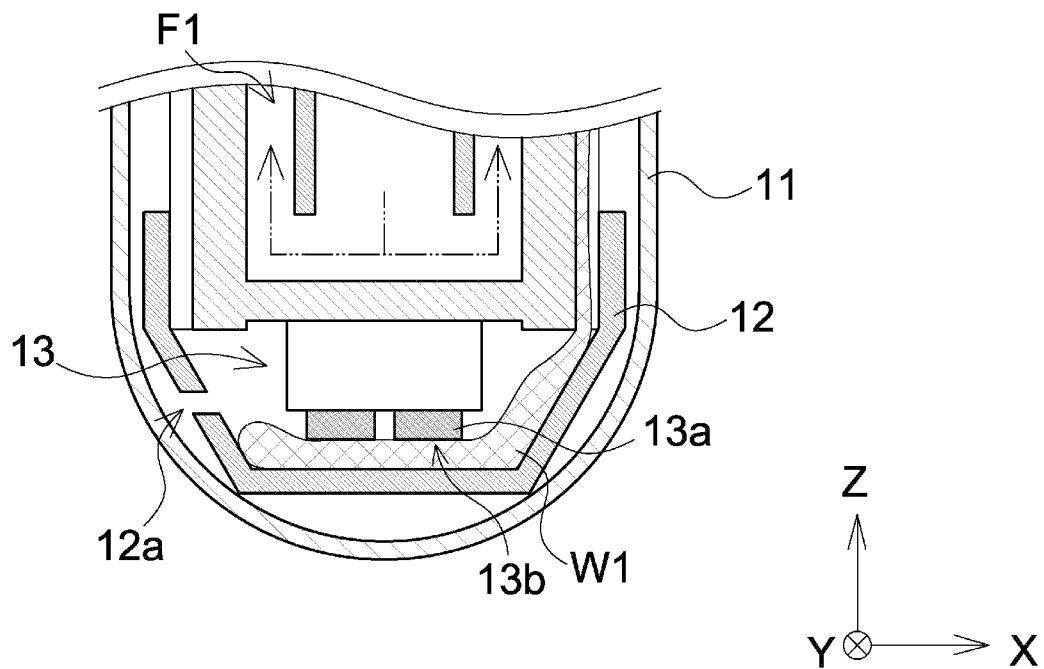
FIG. 5B is an enlarged view of a reservoir of the light irradiation device of FIG. 3.

FIG. 5B is an enlarged view of the reservoir 12 of the light irradiation device 1 of FIG. 3. As shown in FIG. 5B, the leaked liquid W1 that flows through the flow groove 14 and reaches the reservoir 12 disposed at the −Z side flows to the inside of the reservoir 12.

When a certain amount of the leaked liquid W1 is stored inside the reservoir 12, the leaked liquid W1 comes into contact with the detection surfaces 13b of the two electrodes 13a of the detector 13, generating a current between the two electrodes 13a via the leaked liquid W1 and detecting the storage of the leaked liquid W1.

Figure 6A:
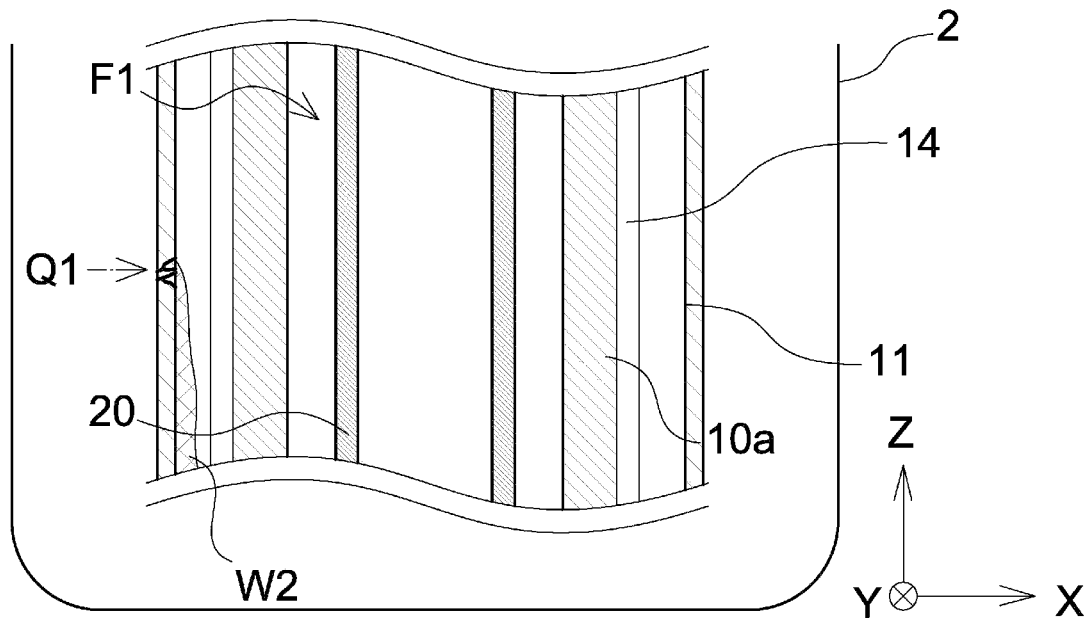
FIG. 6A is an enlarged view of the region A of the light irradiation device of FIG. 3.

Next, the case in which the liquid to be treated enters the inside of the protective tube 11 in the region A in FIG. 1 will be described. FIG. 6A is an enlarged view of the region A of the light irradiation device 1 in FIG. 3. As shown in FIG. 6A, when the light source supporter 10 is accommodated in the protective tube 11 and used to be immersed in the liquid to be treated Q1, if the protective tube 11 is damaged such as a crack, the liquid outside the protective tube 11 enters the protective tube 11 as a leaked liquid W2.

The leaked liquid W2 that has entered the protective tube 11 flows s along the inner wall surface 11p of the protective tube 11 toward the −Z side (downward in the vertical direction).

Figure 6B:
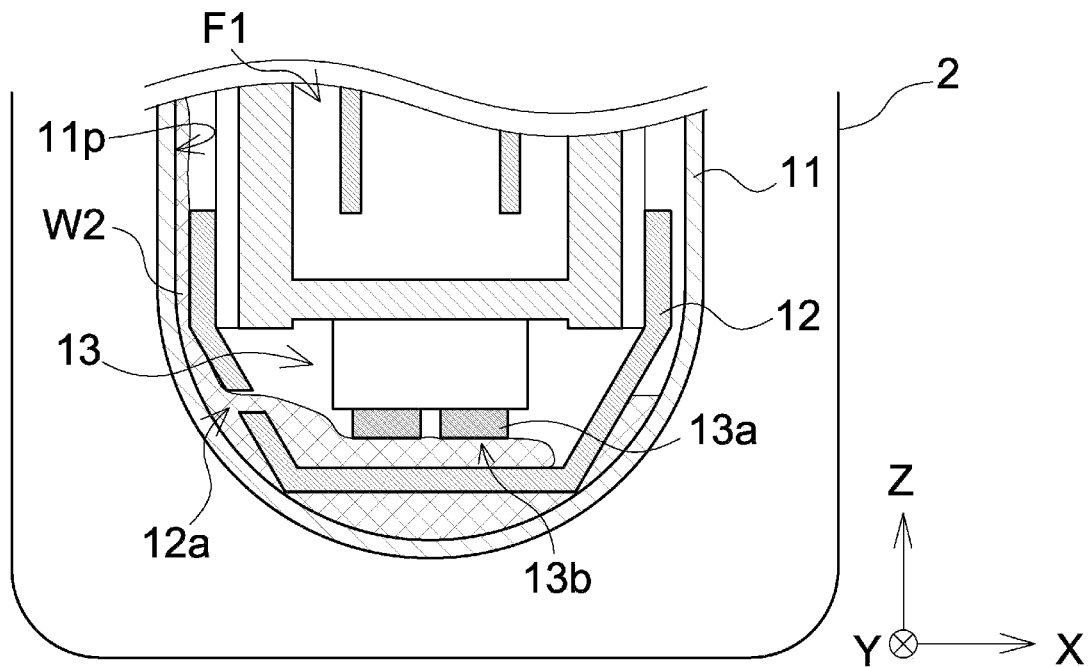
FIG. 6B is an enlarged view of the reservoir of the light irradiation device of FIG. 3.

FIG. 6B is an enlarged view of the reservoir 12 of the light irradiation device 1 in FIG. 3. As shown in FIG. 6B, the leaked liquid W2, which flows along the inner wall surface 11p of the protective tube 11 and reaches the periphery of the reservoir 12 located on the −Z side, flows through the communication hole 12a to the inside of the reservoir 12.

When a certain amount of the leaked liquid W2 stores inside the reservoir 12, the leaked liquid W2 comes into contact with the detection surfaces 13b of the two electrodes 13a of the detector 13, generating a current between the two electrodes 13a via the leaked liquid W2 and detecting the storage of the leaked liquid W2.

As described above, the light irradiation device 1 of the first embodiment detects both the leaked liquid W1 associated with the cooling medium that flows through the inside of the light source supporter 10, and the leaked liquid W2 caused by the damage of the protective tube 11.

Upon the occurrence of both cases of the leaked liquids W1 and W2, the above configuration enables the light irradiation device 1 to detect the leaked liquids W1 and W2 with the detector section 13 by making the leaked liquids W1 and W2 flowing to the reservoir 12 without adhering to the substrates 3b on which the LEDs 3, which are the light-emitting elements, and the wiring patterns are formed.

In addition, positioning the detection surfaces 13b of the electrodes 13a of the detector 13 to face downward in the vertical direction is capable of detecting the leaked liquids W1 and W2 stored in the reservoir 12 at an early stage.

Therefore, upon the occurrence of the leaked liquids W1 and W2 of the cooling medium and the liquid to be treated Q1 in the light irradiation device 1, this configuration is capable of detecting the leaked liquids W1 and W2 safely and quickly, thus stopping the power supply and removing the light irradiation device 1 from the container 2 in the case of occurring the damage and the defect of the light irradiation device 1.

As shown in FIGS. 4A and 4B, the light source supporter 10 has a regular octagonal shape when viewed in the Z-direction on its the outer wall surface 10q on each of which the substrate 3b having the LEDs 3 thereon is mounted, however, the light source supporter 10 can be shaped as a circular, oval, or other polygonal such as quadrilateral or hexagonal.

The configuration of the channel F1 illustrated in FIG. 3, is a mere example, and may be any shape of the channel F1. The direction in which the cooling medium flows is not limited to the direction of the arrow shown in the figure. This also holds true for the configuration of the channel F1 and the direction in which the cooling medium flows described in the drawings after FIG. 3.

The light-emitting elements mounted on the substrate 3b are described as LEDs 3; however other light-emitting elements such as LDs may be arranged, or even phosphor may be mounted among the light-emitting elements. Furthermore, each light-emitting element may be a light-emitting element that emits light other than ultraviolet light such as visible light and infrared light.

The detector 13 of the first embodiment has the detection surfaces 13b of the electrodes 13a, the detection surfaces facing the −Z direction (downward in the vertical direction); however, the detection surfaces 13b may be configured to face any direction including the +Z direction (upward in the vertical direction), the X direction, and Y direction.

The method of detecting the liquid stored in the reservoir 12 may also include, for example, a method of using light refraction. Depending on the method of detection, the detector 13 may be disposed outside the reservoir 12 and may not be provided with the detection surface 13b.

The flow grooves 14 of the first embodiment is the plurality of flow grooves 14 formed at equal intervals in the circumferential direction of the light source supporter 10; however, the flow grooves 14 may be one and may not be formed at equal intervals in the circumferential direction of the light source supporter 10.

Second Embodiment

Hereinafter, the configuration of the second embodiment of the light irradiation device 1 according to the present invention will be described, focusing on the points that differs from those of the first embodiment.

Figure 7A:
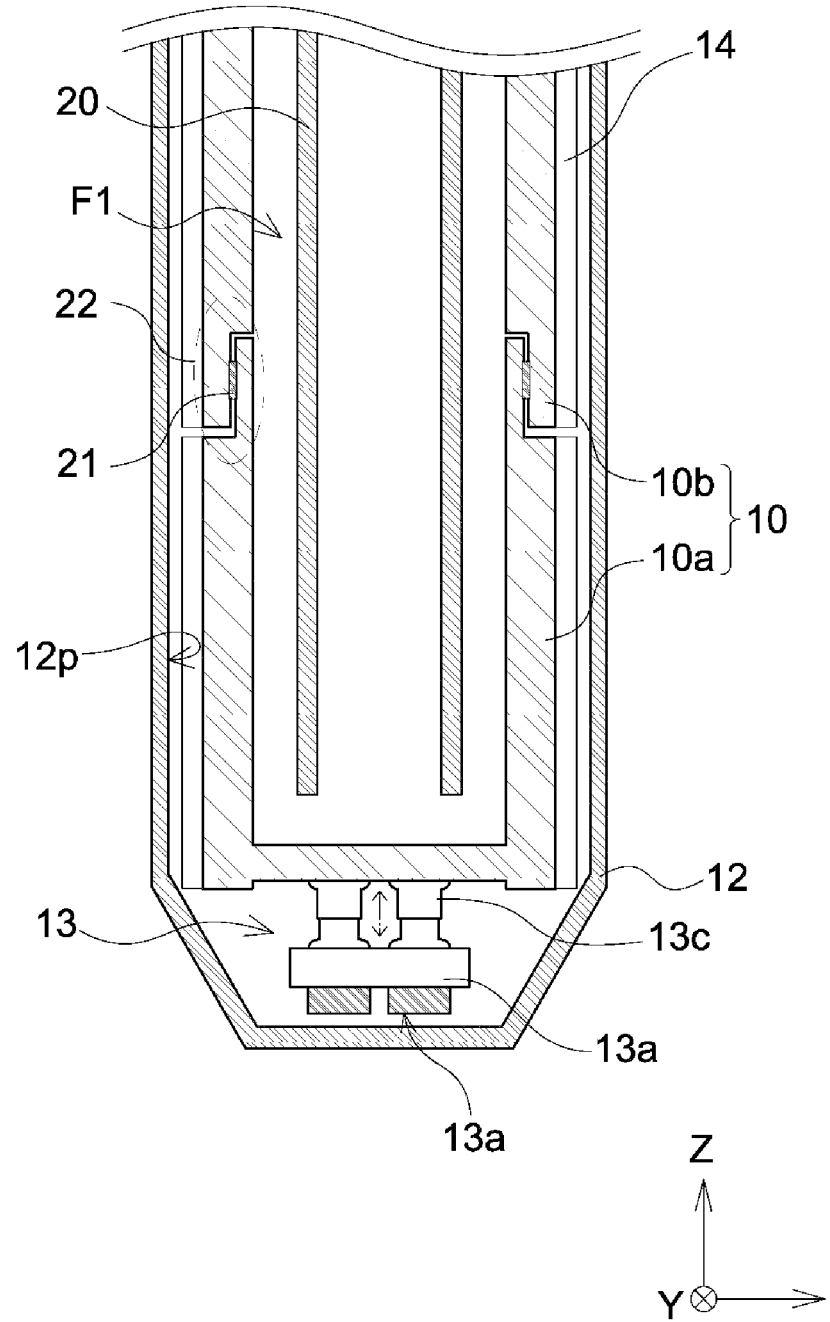
FIG. 7A is a cross-sectional view schematically illustrating an embodiment of a light irradiation device.

FIG. 7A is a cross-sectional view schematically illustrating an embodiment of the light irradiation device 1. As shown in FIG. 7A, the reservoir 12 of the light irradiation device 1 includes a tubular body that is transmissive to light and covers the light source supporter 10, compared to that of the first embodiment.

The material specifically constituting the reservoir 12, which is a tubular body, may include, for example, quartz glass or borosilicate glass, which is transmissive to light and is capable of being immersed in the liquid to be treated Q1.

The detector 13 of the second embodiment is connected to the light source supporter 10 via a sliding member 13c that is deformable in the Z direction. This configuration allows the detection surface 13b of the electrode 13a provided in the detector 13 to readily make in contact with the bottom of the reservoir, and also reduces the load on the bottom of the reservoir 12 during its installation, detecting the leaked liquids W1 and W2 stored in the reservoir 12 more quickly.

The member connecting the detector 13 to the light source supporter 10 may not be the sliding member 13c as long as it can be configured to have a mechanism deformable in the Z-direction, such as a spring or rubber.

The leaked liquid W1, as similar to the first embodiment, flows along the flow groove 14 formed on the outer wall surface 10q of the light source supporter 10 toward the −Z direction (downward in the vertical direction).

The leaked liquid W1 flowing through the flow groove 14 to reach the reservoir 12 located below flows to the inside of the reservoir 12. When a certain amount of the leaked liquid W1 is stored inside the reservoir 12, the leaked liquid W1 comes into contact with the detection surfaces 13b of the two electrodes 13a of the detector 13, generating a current between the two electrodes 13a via the leaked liquid W1 and detecting the storage of the leaked liquid W1.

In the second embodiment, the leaked liquid W2 flows along the inner wall surface 12p of the reservoir 12 toward the −Z direction (downward in the vertical direction).

The leaked liquid W2 flowing along the inner wall surface 12p of the reservoir 12 and stores at the bottom of the reservoir 12. When a certain amount of the leaked liquid W2 is stored at the bottom of the reservoir 12, the leaked liquid W2 comes into contact with the detection surfaces 13b of the two electrodes 13a of the detector 13, generating a current between the two electrodes 13a via the leaked liquid W2 and detecting the storage of the leaked liquid W2.

As described above, the light irradiation device 1 of the second embodiment detects both the leaked liquid W1 associated with the cooling medium that flows through the inside of the light source supporter 10, and the leaked liquid W2 caused by the damage of the protective tube 11.

It is noted that the reservoir 12 of the second embodiment is a tubular body configured to cover the entire light irradiation device 1, thereby the light irradiation device 1 can be used to be immersed in the liquid to be treated without providing an additional component such as the protective tube 11.

Figure 7B:
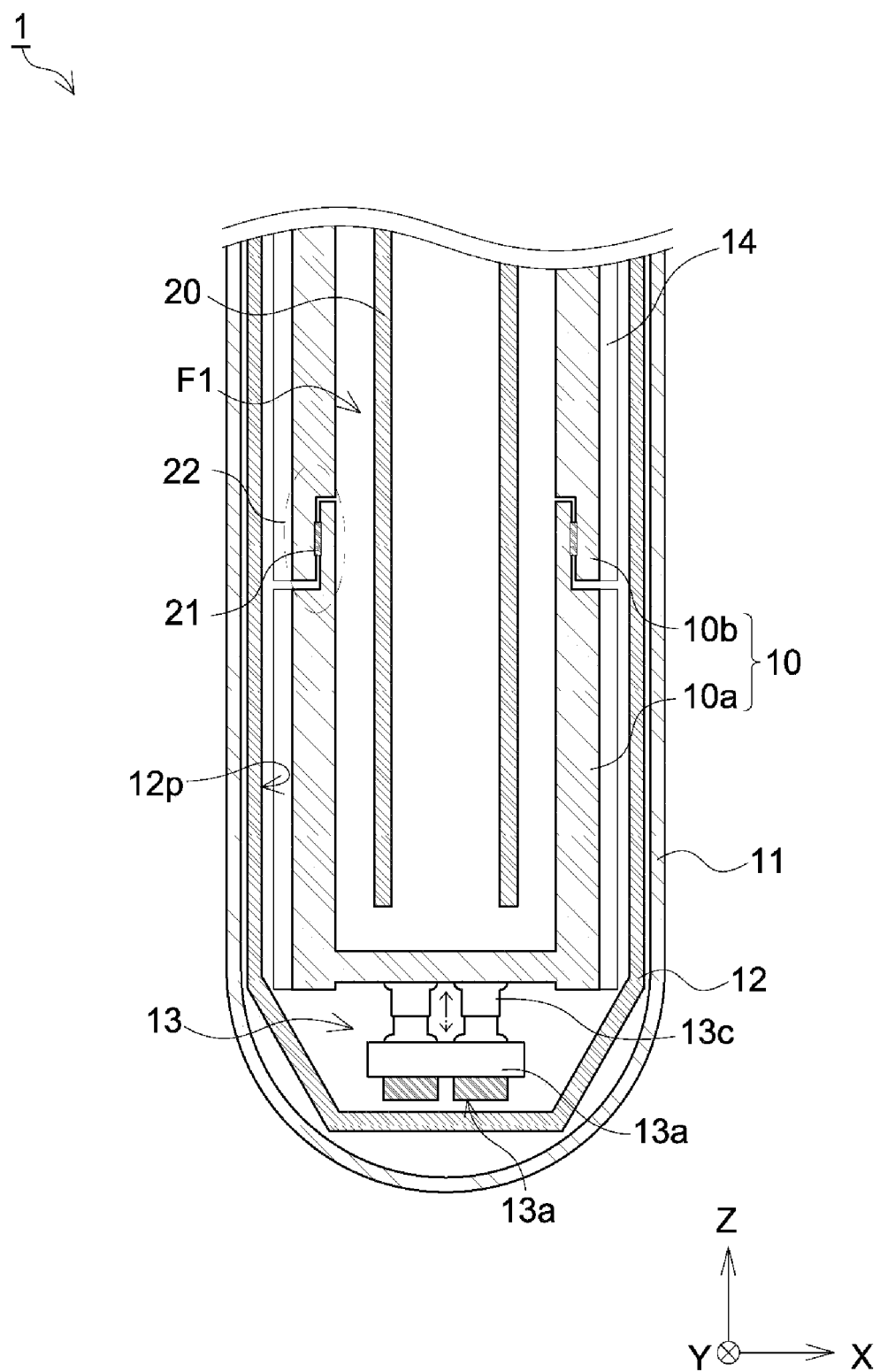
FIG. 7B is a cross-sectional view schematically illustrating one embodiment of a light irradiation device.

FIG. 7B is a cross-sectional view schematically illustrating one embodiment of the light irradiation device 1. As shown in FIG. 7B, the light irradiation device 1 of the second embodiment may be provided with the protective tube 11 that entirely accommodates the light source supporter 10 and the reservoir 12. The material constituting the protective tube 11 may include, for example, quartz glass or borosilicate glass, as described above.

The above configuration, in which the protective tube 11 is provided, enables the light irradiation device 1 to be used to be immersed in the liquid to be treated Q1, regardless of the material constituting the reservoir 12 of the second embodiment.

Another Embodiment

Hereinafter, another embodiment will be described.

Figure 8:
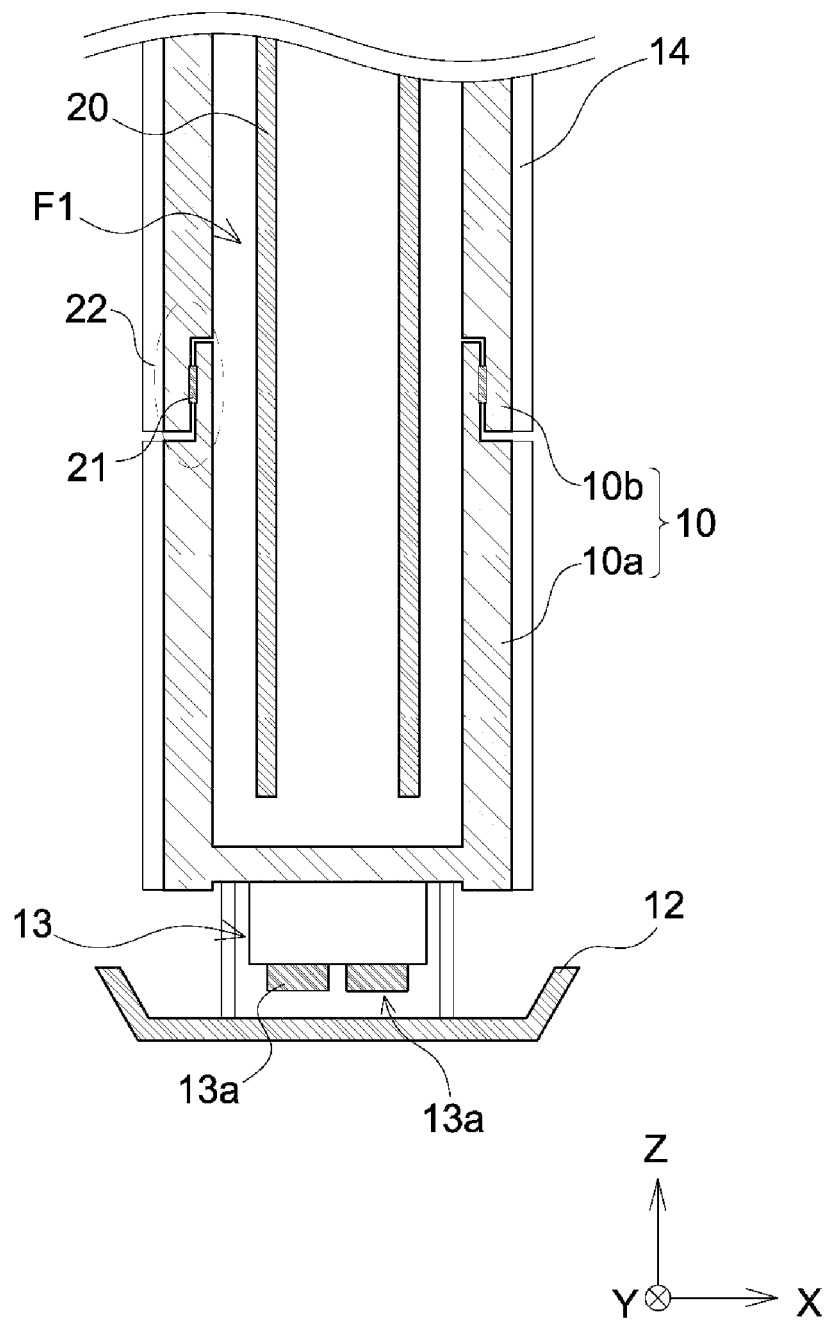
FIG. 8 is a cross-sectional view schematically illustrating another embodiment of a light irradiation device.

<1> FIG. 8 is a cross-sectional view schematically illustrating another embodiment of the light irradiation device 1. As shown in FIG. 8, the light irradiation device 1 of the present invention is not necessarily provided with the protective tube 11, for example, when the object to be treated is irradiated with light from the outside thereof. The reservoir 12 may be disposed apart from the first end of the light source supporter 10 without covering the first end of the light source supporter 10.

<2> The configuration provided in the light irradiation device 1 described above is merely an example. The present invention is not limited to each of the illustrated configurations.

REFERENCE SIGNS LIST

1 Light irradiation device
2 Container
3 LED
3*b* Substrate
10 Light source supporter
10*a*, 10*b* Connection member
10*p* Inner wall surface
10*q* Outer wall surface
10*x* Axis
11 Protective tube
11*p* Inner wall surface
12 Reservoir
12*a* Communication hole
12*p* Inner wall surface
13 Detector
13*a* Electrode
13*b* Detection surface
13*c* Sliding member
14 Flow groove
20 Cylinder
20*q* Outer wall surface
21 O-ring
22 Connection section
F1 Channel
L1 Ultraviolet light
Q1 Liquid to be treated
W1, W2 Leaked liquid

The invention claimed is:

1. A light irradiation device comprising:
a light-emitting element;
a cylindrical light source supporter having an outer wall surface on which the light-emitting element is disposed, and including a channel that is formed inside the light source supporter to allow cooling medium to flow through;
a flow groove that is formed on the outer wall surface in an axial direction of the light source supporter;
a reservoir that is communicated with the flow groove at a first end of the light source supporter in the axial direction and that is configured to allow liquid to be stored; and
a detector that is configured to allow the liquid stored in the reservoir to be detectable,
wherein the first end of the light source supporter is located at a position downward in a vertical direction relative to a second end of the light source supporter, the reservoir being disposed at the first end in the axial direction thereof.

2. The light irradiation device according to claim 1, wherein the detector includes a detection surface that detects the liquid when the liquid is in contact with the detection surface, and the detection surface is located to face downward in the vertical direction.

3. The light irradiation device according to claim 1, further comprising a plurality of substrates on the outer wall surface, the light-emitting element being mounted on the substrates, wherein the flow groove is formed between the substrates that are adjacent each other in a circumferential direction of the light source supporter.

4. The light irradiation device according to claim 1, further comprising a plurality of flow grooves are formed in a circumferential direction when viewed in the axial direction of the light source supporter.

5. The light irradiation device according to claim 1, wherein the reservoir includes a receiving portion having a cylindrical shape with an inner bottom, the receiving portion being configured to cover the first end of the light source supporter in the axial direction.

6. The light irradiation device according to claim 1, wherein the reservoir includes a tubular body that is transmissive to light and covers the light source supporter.

7. The light irradiation device according to claim 6, wherein the light source supporter is connected to a member that is deformable to the detector in the axial direction.

8. The light irradiation device according to claim 1, further comprising a protective tube that is transmissive to light, and that accommodates the light source supporter and the reservoir;
wherein the reservoir includes a communication hole that communicates a space in which the liquid is stored with a space inside the protective tube.

9. The light irradiation device according to claim 2, further comprising a plurality of substrates on the outer wall surface, the light-emitting element being mounted on the substrates, wherein the flow groove is formed between the substrates that are adjacent each other in a circumferential direction of the light source supporter.

10. The light irradiation device according to claim 2, further comprising a plurality of flow grooves are formed in a circumferential direction when viewed in the axial direction of the light source supporter.

11. The light irradiation device according to claim 2, wherein the reservoir includes a receiving portion having a cylindrical shape with an inner bottom, the receiving portion being configured to cover the first end of the light source supporter in the axial direction.

12. The light irradiation device according to claim 2, wherein the reservoir includes a tubular body that is transmissive to light and covers the light source supporter.

13. The light irradiation device according to claim 12, wherein the light source supporter is connected to a member that is deformable to the detector in the axial direction.

14. The light irradiation device according to claim 2, further comprising a protective tube that is transmissive to light, and that accommodates the light source supporter and the reservoir;
wherein the reservoir includes a communication hole that communicates a space in which the liquid is stored with a space inside the protective tube.

* * * * *